US00PP08470P

United States Patent [19]

Zaiger et al.

[11] Patent Number: Plant 8,470

[45] Date of Patent: Nov. 23, 1993

[54] PLUM COT TREE "FLAVORELLA"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 997,510

[22] Filed: Dec. 28, 1992

[51] Int. Cl.[5] ..... A01H 5/00

[52] U.S. Cl. ..... Plt./38.1

[58] Field of Search ..... Plt./38.1, 39

*Primary Examiner*—James R. Feyrer

[57] ABSTRACT

Our new and distinct variety of Plum Cot tree (Plum-×Apricot) has the following unique combination of desirable features that are outstanding in a new variety.

1. Heavy and regular production of medium size fruit.
2. Fruit with excellent flavor and eating quality.
3. Relatively uniform ripening of fruit throughout the tree.
4. Fruit with a high degree of soluble solids (Average 14.6 Brix).
5. Vigorous semi-upright growth.
6. Fruit, although mild and sweet, having a good balance between sugar and acid with a creative taste between Apricot and Plum.
7. Early maturity of the fruit.

1 Drawing Sheet

ORIGIN OF THE VARIETY

Our new variety of Plum Cot tree was originated by us in our experimental orchard, located near Modesto, Calif., as a selected seedling which originated from an open pollinated seedling selection with the identification number 35EA376. The seedling 35EA376 originated from a large group of open pollinated Red Beaut Plum (U.S. Plant Pat. No. 2,539) seedlings. The large number of seedlings from which the present new variety of Plum Cot was selected were grown under careful observation by use and gave many and varying characteristics, one such seedling, having been especially desirable as to its fruit characteristics described above was selected for asexual reproduction and commercialization.

ASEXUAL REPRODUCTION OF THE VARIETY

The present new variety of Plum Cot tree was asexually reproduced by budding, as performed by us in the experimental orchard located near Modesto, Calif., shows that all characteristics of the tree and its fruit come true to the original tree and are established and transmitted through succeeding propagations.

SUMMARY OF THE VARIETY

Our new and distinct variety of Plum Cot tree (Plum-×Apricot) which is of large size, vigorous, medium dense, semi-upright growth, and a regular and productive bearer of medium size, yellow flesh, early maturing, clingstone fruit with excellent flavor and eating quality. The fruit is further characterized by having very short, soft pubescence, similar to an apricot but shorter in length, relatively uniform ripening through-out the tree, a pronounced aroma, mild sweet flavor with a creative taste between apricot and plum.

DESCRIPTION OF THE PHOTOGRAPHS

The accompanying photographic illustrations show typical specimens of the fruit and foliage of our new Plum Cot variety. The upper and lower surface of the leaves being illustrated, an exterior and a sectional view of the fruit being divided in the suture plane to reveal flesh coloration, pit cavity, and a stone remaining in place. The photographs were taken shortly after being picked (shipping ripe) and the colors are as nearly true as is reasonably possible in a color representation of this type.

DESCRIPTION OF THE VARIETY

The following is a detailed botanical description of the new and distinct variety of Plum Cot tree, its flowers, foliage and fruit as based on observations of the variety grown near Modesto, Calif., with color terminology (except those in common terms) in accordance with Reinhold Color Atlas by A. Korneruf and J. H. Wanschser.

Tree:
- *Size.*—Large.
- *Vigor.*—Vigorous.
- *Growth.*—Semi-upright.
- *Density.*—Medium dense.
- *Bearer.*—Regular.
- *Production.*—Productive.

Trunk:
- *Size.*—Medium to large.
- *Surface.*—Medium shaggy.
- *Color.*—Grayish brown to brown (6-E-4) to (6-E-6).

Branches:
- *Size.*—Medium stocky.
- *Surface.*—Smooth to medium rough.
- *Lenticels.*—Numerous. Medium size.
- *Color.*—New growth — reddish brown. Old growth — brown to grayish brown.

Leaves:
- *Size.*—Large. Average length — 5½". Average width — 2".
- *Texture.*—Smooth.
- *Form.*—Varies from elliptical to oblanceolate.
- *Margins.*—Finely serrate.
- *Thickness.*—Medium.
- *Petiole.*—Average length — 1¼". Medium thickness.
- *Glands.*—Globose. Number varies from 1 to 8. Average number 4. Medium size. Located on upper portion of petiole and lower portion of leaf blade.

*Color.*—Upper surface — grayish green (27-E-5) to dark green (27-F-5). Lower surface — dull green (27-E-3) to grayish green (27-E-4).

Flower buds:

*Size.*—Medium.

*Length.*—Medium.

*Pubescence.*—Pubescent.

Flowers:

*Blooming period.*—Feb. 26, 1991 to Mar. 3, 1991. Varies slightly due to climatic conditions.

*Size.*—Medium.

*Pollen.*—Present.

*Color.*—White.

*Pistil.*—Pubescent.

Fruit:

*Maturity when described.*—Firm ripe.

*Date of first picking.*—Jun. 5, 1991.

*Date of last picking.*—Jun. 11, 1991.

*Size.*—Medium. Average diameter axially 2¼". Average transversely in suture plane 2¼". Average diameter at right angles to suture plane 2⅛".

*Form.*—Globose — nearly symmetrical.

*Suture.*—Very shallow — extends from base to apex.

*Ventral surface.*—Rounded — nearly smooth.

*Apex.*—Usually slightly retuse, with very small pistil point in center of flattened area.

*Cavity.*—— to very slightly elongated in suture plane. Average depth —⅜". Average breadth — ½".

Skin:

*Thickness.*—Medium to thin.

*Texture.*—Medium — tenacious to flesh.

*Down.*—Scant — very short.

*Tendency to crack.*—None.

*Color.*—Yellow to apricot yellow (5-A-6) to (5-B-6).

Flesh:

*Color.*—Yellow to golden yellow (5-A-4) to (5-A-5).

*Texture.*—Firm.

*Fibers.*—Few, small, tender.

*Ripens.*—Evenly.

*Flavor.*—Excellent. Mild — sweet, good balance between acid and sugar.

*Juice.*—Moderate.

*Aroma.*—Pronounced.

*Eating quality.*—Excellent.

Stone:

*Type.*—Clingstone.

*Size.*—Medium. Average length — 1 1/16". Average width — 13/16 ". Average thickness — 5/16".

*Form.*—Varies from ovoid to obovoid.

*Sides.*—Mostly equal, some unequal.

*Ridges.*—Small ridges extending on each side of suture.

*Surface.*—Lightly pitted throughout.

*Apex.*—Varies from rounded to slight point.

*Base.*—Usually rounded — varies from round to straight.

*Tendency to split.*—None.

*Color.*—Varies from light brown to reddish brown (8-D-5) to (9-D-5).

Use: Dessert.

*Market.*—Local and long distance.

Keeping quality: Good.

Shipping quality: Good.

The new and distinct variety of Plum Cot tree, its flowers, fruit and foliage may vary in slight detail due to soil type, climatic conditions and cultural practices under which the variety may be grown; the present description is that of the new variety grown, under the ecological conditions prevailing near Modesto, Calif.

The following is claimed:

1. A new and distinct variety of Plum Cot tree, substantially as illustrated and described, characterized by its large size, vigorous, semi-upright growth and a productive and regular bearer of medium size, early maturing, clingstone fruit; the fruit is further characterized by having a good balance between sugar and acid with excellent flavor and eating quality and having firm flesh with the ability to ship to long distance markets.

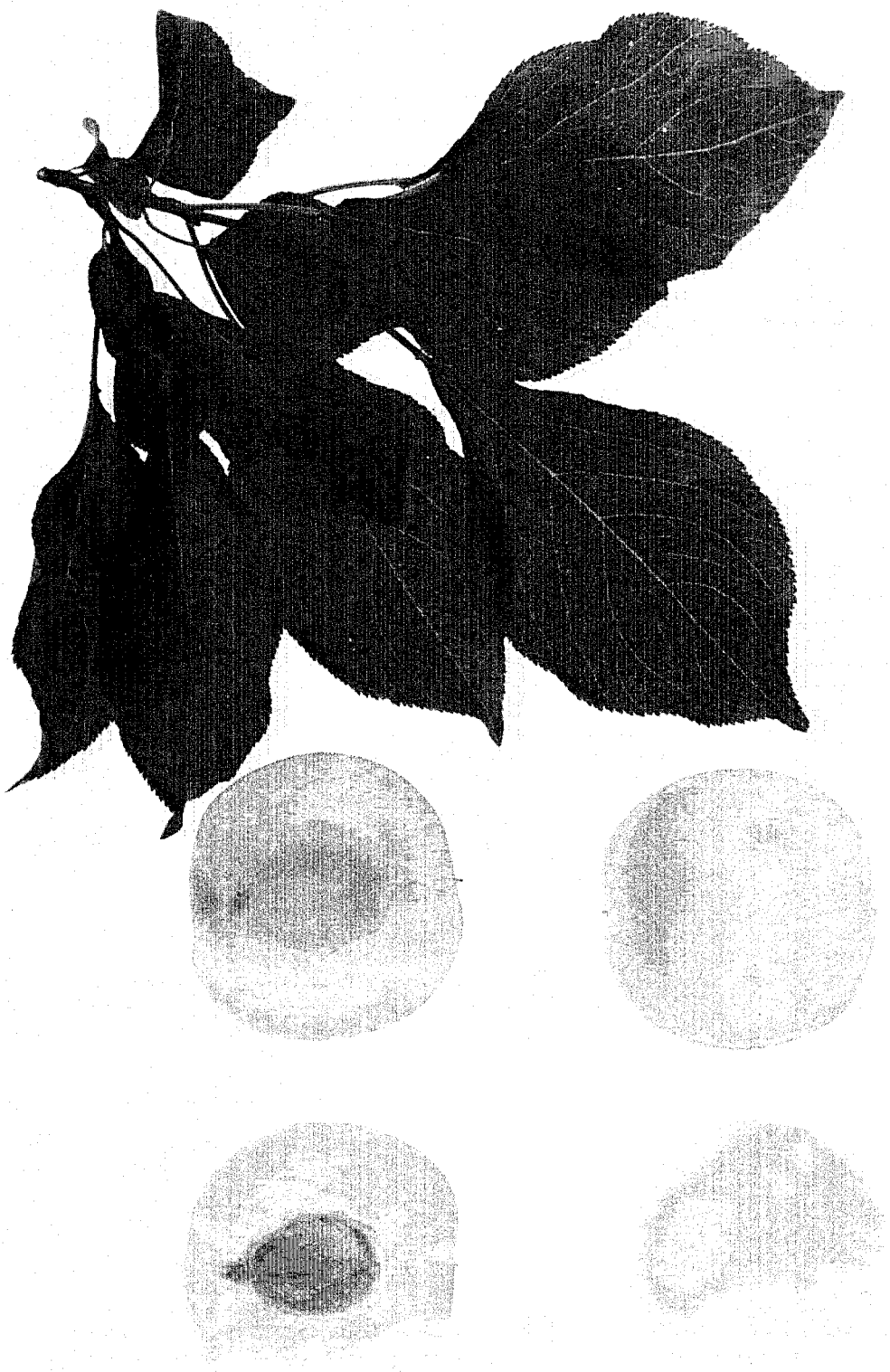

* * * * *